United States Patent [19]

Lee et al.

[11] Patent Number: 5,324,515
[45] Date of Patent: Jun. 28, 1994

[54] COSMETIC MATERIAL OBTAINED FROM A LACTIC ACID FERMENTATION BROTH

[75] Inventors: Ho Lee, Seoul; Seung G. Yang, Kwacheon, both of Rep. of Korea

[73] Assignee: Pacific Corporation, Seoul, Rep. of Korea

[21] Appl. No.: 959,566

[22] Filed: Oct. 13, 1992

[30] Foreign Application Priority Data

Oct. 22, 1991 [KR] Rep. of Korea ............... 91-18556

[51] Int. Cl.$^5$ ............... A61K 35/00; C12P 7/56
[52] U.S. Cl. ............... 424/115; 435/139; 435/272; 435/853
[58] Field of Search ............... 424/115; 435/139, 272, 435/853

[56] References Cited

U.S. PATENT DOCUMENTS 4,524,136  6/1985  Lee et al. ............... 435/139

Primary Examiner—Paul J. Killos
Attorney, Agent, or Firm—Nixon & Vanderhye

[57] ABSTRACT

The present invention provides a cosmetic material which consists of a disintegration phase which is obtained by harvesting lactic acid bacterial cells from the lactic fermentation broth, disintegrating the cells, subjecting the broken cells to centrifugation to give a supernatant and adding to the supernatant 10 μM of 500 μM of at least one metal ions followed by filtration to obtain a filtrate and an extraction phase which is obtained by extracting cell pellets precipitated by the centrifugation step in (a) with water or an organic solvent and a non-ionic surfactant and subjecting the extract to filtration to obtain a filtrate. The cosmetic material of the present invention exhibits properties of scavenging harmful oxygen species, reinforcing DNA repair system of the skin and reinforcing immune systems of the skin. It further comprises mannitols or flavonoids in order to enhancing its ability of scavenging harmful oxygen species.

6 Claims, 2 Drawing Sheets

COSMETIC MATERIAL OBTAINED FROM A LACTIC ACID FERMENTATION BROTH

BACKGROUND OF THE INVENTION

1. Field of the Invention

The present invention relates to a functional cosmetic material. More particularly, it relates to a functional cosmetic material obtained from a lactic acid fermentation broth, which exhibits an active oxygen species-scavenging, a DNA repair system-reinforcing and an immune system-reinforcing properties.

2. Description of the Prior Art

Recent research on the cell biology leads to a development of functional cosmetics for, for example, retarding aging in humans. One aspect of the development of functional cosmetics is to provide cosmetics which have an ability of scavenging harmful active oxygen species. The active oxygen species are byproducts generated from the oxygen metabolism in humans and other mammals, and include, for example, superoxide radical ($O_2-$), hydroxyl radical(.OH) and singlet oxygen ($^1O_2$). These active oxygen species have critical roles in lipid superoxidation, protein denaturation and nucleic acid mutation. Although the harmful active oxygen species are continually destroyed by protective enzymes, for example, superoxide dismutase, catalase and glutathione peroxidase, such defenses are not 100% efficient, and particularly aging and environmental stimuli make the defenses by the protective enzymes less efficient. Thus chemical destruction of cells can result, an example of the cell damage caused by the oxygen species is damage to DNA, which virtually may resulted in a formation of cancer (Leibvitz B. E. & Siegel B. W. 1980, J. Gerontol. 35:45). Active oxygen species also are related to inflammation (William F. P. et al., Proc. Natl. Acad. Sci. USA 77:1159 (1980)) and to various diseases (Chikako Nishigen M. D. et al., J. Invest. Derma. 1989).

The raising needs for an artificial active agent which can scavenge the harmful oxygen species lead to a development of cosmetic materials containing superoxide dismutase, flavonoids and lactoferins. However, these active components have a drawback, when used in cosmetic compositions for the skin, that the superoxide dismutase is sparingly soluble in oils and unstable as well as is poor in its adsorption and absorption to the skin. Further, lactoferins have a drawback that their production from milk by extraction methods is complicate and the yield is low.

Another aspect of the development of functional cosmetics is to find out an agent which can reinforce the DNA repair systems in the skin. DNA is a cell's genetic material which carries genetic information and plays most important roles in the survival of cells. DNA molecules are always exposed to various sources causing a damage thereto and also have specific enzymatic mechanisms to repair damaged sites. However, continued environmental stresses and aging make the DNA repair by the enzymatic machinery less efficient. The damaged cells, which are not repaired, may become cancerous and cause abnormally high skin cell death and skin diseases (V. A. Bohr et al., 1989, Laboratory Investigation 61(2):143). Particularly, excess exposure to UV light of sunlight leads to a formation of thymine dimer which causes cell death and DNA mutation.

So far some cosmetic materials are developed as an anti-mutation agent in order to impart DNA repair ability to cosmetic compositions and such cosmetic materials include, for example, specific plant extracts, placenta extracts and Actinomycetes strain extracts. However, the extracts derived from plants and Actinomycetes strains have a weak substantivity to the skin and may induce adverse effects. Placenta extracts have no such problems, but their production is limited.

Another aspect of the development of the functional cosmetic compositions is to provide an agent which can reinforce the immune systems of the skin. The immune system is a defence machinery of a living body, which maintains and protects the living body from the environment containing a large variety of infectious microbial agents. Aging considerably weaken the capacity of the immune system, resulting in various skin diseases (Atsushi Uchida, Fragrance J., 19C9):29 (1991). However, so far no satisfactory agent for enhancing the function of the dermal immune systems, which can be used in cosmetic compositions, is proposed.

By the way, it has been known that an useful moisturizing factor can be obtained from skim milk. Particularly, U.S. Pat. No. 4,524,136 discloses a process for preparing a cosmetic material comprising the steps of simultaneously carring out in skim milk the processes of lactic acid fermentation by lactic acid bacteria and decomposition of casein by proteases; and simultaneously carrying out the processes of sterilization of lactic acid bacteria and inactivation of proteases to produce a cosmetic material. However, the said patent is based on a fact that lactates is an useful moisturizing factor and its purpose is to provide a transparent cosmetic material which can be easily absorbed and adsorbed to the skin, and therefore, has no relation to the present invention.

The present inventors had found out that there may be obtained a cosmetic material, which is useful to scavenge harmful oxygen species and has moisturizing property, by fermenting a lactic acid bacteria in skim milk or powdered skim milk cantaining metal ions and proteases and treating the harvested cells (Korean Patent Application No. 90-6419). However, the cosmetic material obtained by the method described in said patent application is insufficient in its ability of reinforcing the DNA repair system. Moreover, the method is less economical of cost and of DNA repair-reinforcing efficacy of the product because it uses only supernatant obtained from centrifugation of the broken cells.

Therefore, there remains a need for a cosmetic material which shows a harmful active oxygen species-scavenging, a DNA repair system-reinforcing and an immune system-reinforcing properties as well as shows good compatiability with and absorption to the skin, and less irritate the skin.

SUMMARY OF THE INVENTION

Thus, one object of the invention is to provide a cosmetic material exhibiting properties of scavenging harmful oxygen species, of reinforcing DNA repair system and of reinforcing immune system, which consists of (a) a disintegration phase which is obtained by harvesting lactic acid bacterial cells from the lactic fermentation broth, disintegrating the cells, subjecting the broken cells to centrifugation to give a supernatant and adding to the supernatant 10 $\mu M$ to 500 $\mu M$ of at least one metal ions followed by filtration to give a filtrate and (b) an extraction phase which is obtained by extracting cell pellets, which are resulted from the centrifugation step in (a), with water or an organic solvent and a non-ionic surfactant and subjecting the extract to filtration to give filtrate.

Another object of the invention is to provide a cosmetic material exhibiting a harmful oxygen species-scavenging, a DNA repair system-reinforcing and an immune system-reinforcing properties, which consists of (a) a disintegration phase which is obtained by harvesting the lactic acid bacterial cells from the lactic fermentation broth, disintegrating the cells, subjecting the broken cells to centrifugation to give a supernatant, and adding to the supernatant 10 μM to 50 μM of at least one metal ions followed by filtration to give a filtrate, (b) an extraction phase which is obtained by extracting cell pellets with water or an organic solvent and a non-ionic surfactant and subjecting the extract to filtration to give a filtrate and (c) a low molecular harmful oxygen species scavenger selected from mannitol and flavonoids.

A more complete appreciation of the invention, and many of the additional advantages thereof, will be readily perceived as the said invention becomes better understood by reference to the following detailed description of the invention. Other objects, advantages and features of the present invention will also become apparent to those skilled in the art from the following descriptions.

DETAILED DESCRIPTION OF THE INVENTION

Figure 1:
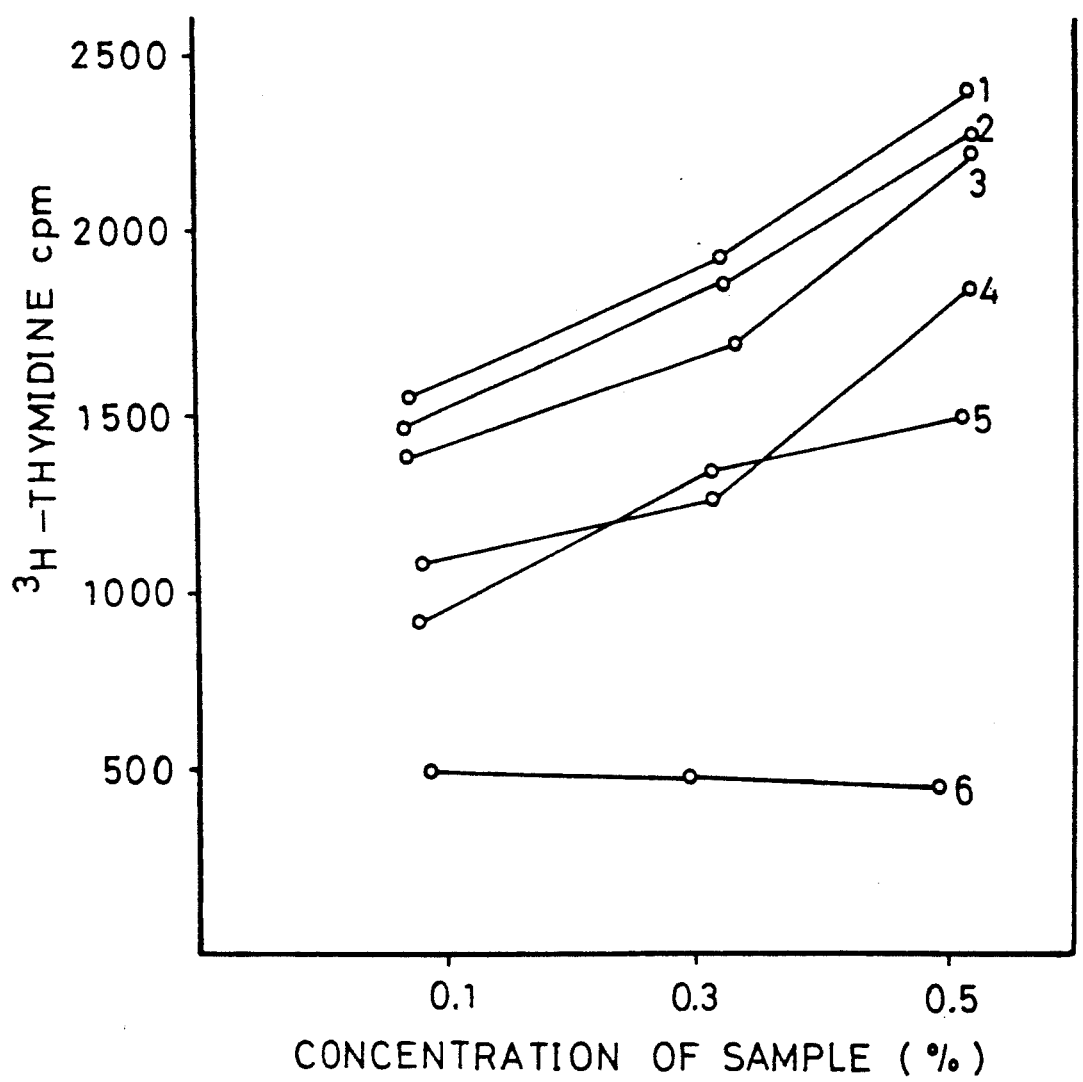
FIG. 1 is a graph showing the action of the cosmetic material according to the invention of reinforcing the DNA repair systems of the skin.

Lactic acid bacteria useful in the present invention include strains of Lactobacillus genus such as *Lactobacillus bulgaricus, L. acidophilus, L. helveticus, L, casei* and strains of Streptococcus genus such as *Streptococcus thermophilus*.

The medium for lactic acid fermentation, which is useful in the present invention, may be selected from the known media which are commonly used for lactic acid fermentation, and may include, for example, skim milk, skim milk powder, MRS broth medium (Difco) and Rogosa broth medium (Difco).

Lactic acid bacteria may be inoculated into the medium to a concentration of 1 to 5%. The lactic fermentation by lactic acid bacteria is usually carried out at 35° to 40° C. for 20 to 25 hours. It is preferable to add proteases to the medium in order to decompose casein formed during the lactic fermentation. Both neutral and acid protease can be used.

Harvesting the lactic acid bacterial cells from the fermentation broth may be accomplished by known methods, for example, a centrifugation at 6000×g for 30 minutes. The harvested cells are washed several times with a physiological saline (0.9% Nacl) or 50 mM potassium phosphate buffer (pH 7.5).

The washed cells may be disintegrated by known methods. Preferably, the cells are disintegrated by using dyno mill with glass beads of 0.1 mm diameter or by methods described in Brian Austin et al., 1981, *Manual of Methods of General Bacteriology* published by ASM.

The broken cells are centrifuged at 15000 g for 30 minutes and 10 to 500 μM of at least one metal ions are added to the supernatant. The solution is filtered with an ultrafilter having cut off of 10,000 dalton. The resulting filtrate is referred to as "disintegration phase". The metal ions added to the supernatant are bivalent metals selected from the group consisting of Cu, Fe, Mn, Mg, Zn and Ni. The metals are present in the form of slats with inorganic or organic acids, for example, sulfates, phosphates, chlorides, bromides and citrates. The inorganic salts, particularly sulfates are preferably employed. The metal salts may be used single or in mixtures thereof.

Besides, cell pellets resulted from the centrifugation of the broken cells are extracted with water or a polar organic solvent selected from diluted ethanol or methanol plus a non-ionic surfactant. The water or polar organic solvent is used in an amount of 20 to 50 volume times the weight of the cell pellets. The amount of the non-ionic surfactant used may between 0.01 and 0.1% (w/v). The extraction may be effected by standing for 2 to 5 days or heating for 30 min to 3 hours. The extract is filtered with an ultrafilter having cut off of 10,000 dalton. The resulting filtrate is referred to as "extraction phase".

The non-ionic surfactants may be selected from the known ones which are commonly used in cosmetic compositions and may include, for example, TWEEN 20 (polyoxyethylene (20) sorbitan monolaurate), TWEEN 60 ( polyoxyethylene (60) sorbitan monostearate), TWEEN 80 (polyoxyethylene (80) sorbitan monooleate) and polyoxyethylene (23) lauryl ether.

The weight ratio of the disintegration phase to extraction phase contained in the cosmetic material according to the invention varies between 10:1 and 1:10, preferably 2:1 and 1:2, and most preferably is 2:1.

The cosmetic material according to the invention comprises, in addition to the disintegration phase and extraction phase, a low molecular weight active oxygen scavenger selected from mannitols and flavonoids in order to enhance its action of scavenging harmful oxygens. The amount of the scavenger added to the cosmetic material usually varies between 10 μmole and 1 mmole.

The term "disintegration phase" employed in the specification and claims of the application means a solution which is obtained by harvesting lactic acid bacterial cells from the lactic fermentation broth, disintegrating the cells, subjecting the broken cells to centrifugation to give a supernatant and adding to the supernatant 10 μM to 500 μM of at least one metal ions followed by filtration to obtain a filtrate. And the term "extraction phase" employed in the specification and claims means a solution which is obtained by harvesting lactic acid bacterial cells from the lactic fermentation broth, disintegrating the cells, subjecting the broken cells to centrifugation to give cell pellets and extracting the cell pellets with water or a polar organic solvent plus a non-ionic surfactant followed by filtration to obtain a filtrate.

The cosmetic material shows excellent properties of scavenging the harmful oxygen species and reinforcing the DNA repair system and skin immune system.

The cosmetic material according to the invention may be incorporated in the conventional cosmetic compositions in an amount of 0.01 to 1.0% by weight based on the cosmetic composition. The cosmetic composition may be, but not intended to limit, a skin-care cosmetic composition such as skin lotions, toilet waters, astringents, facial creams, lotions, body lotions, cleansing creams, cleansing lotions, hand lotions, essences, facial packs or massage creams and a hair-care cosmetic composition such as shampoos, hair rinses, hair sprays, hair creams or hair lotions.

The present invention being generally described, a more complete understanding can be attained by reference to examples which are provided herein for purposes of illustration only, and are not intended to limit the invention in any way.

EXAMPLE 1

After sterilizing and cooling a medium, which was prepared by adding 1.0% of bacterial neutral protease (activity: 8000 $(PU)_{Tyr}{}^{Cas.F.R.}/g$) of source of *Bacillus subtilis* to 1 l of skim milk (10% as solids-non-fat content) and reacting the mixture at 45° C. for 30 min, in a conventional manner, 2-3% of starter of *Lactobacillus bulgaricus* was inoculated thereto. After culturing at 40° C. for 48 hours, the culture solution was centrifuged at 6000×g for 20 minutes to recover the cells.

The cells were suspended to a concentration of 10% in 0.9% aqueous NaCl solution and disintegrated with a dyno mill having 0.1 mm glass beads (3000 rpm) at a rate of 3 l/hr. The resulting suspension was subjected to centrifugation at 15000×g for 30 min and 10 μM of $MnSO_4$ was added to the supernatant. The mixture was filtered with an ultrafilter NMWC 10,000 (cut off of 10,000 dalton, Whatman) to obtain 250 ml of filtrate. The filtrate is referred to as "disintegration phase".

Besides, to the cell pellets resulted from the above centrifugation step were added 20 times volume of water and 0.01% (w/v) of TWEEN 80(polyoxyethylene (80) sorbitan monooleate) and extraction was effected under heating for 3 hours. The extract was filtered with an ultrafilter NMWC 10,000 (Whatman) to obtain 150 ml of filtrate, which is referred to as "extraction phase".

EXAMPLE 2

By following the procedure in Example 1 except that 2-3% of starter of *Streptococcus thermophilus* was inoculated to MRS Broth medium (Difco), there was obtained a supernatant. After adding 100 μM of $FeSO_4$ and 100 μM of $NiSO_4.6H_2O$, the mixture was filtered with an ultrafilter NMWC 10,000 (Whatman) to obtain 200 ml of filtrate which is referred to as "disintegration phase".

Besides, to the cell pellets resulted from centrifugation were added 30 times volume of 70% ethanol and 0.05%(w/v) of TWEEN 20 (polyoxyethylene (20) sorbitan monooleate) and extraction was effected under heating for 2 hours. The extract was filtered with an ultrafilter NMWC 10,000 (Whatman) to obtain 180 ml of filtrate, which is referred to as "extraction phase".

EXAMPLE 3

By following the procedure in Example 1 except that 2-3% of starter of *Lactobacillus helveticus* was inoculated to ROGOSA Broth medium (Difco), there was obtained a supernatant. After adding 200 μM of $ZnSO_4$, the mixture was filtered with an ultrafilter NMWC 10,000 (Whatman) to obtain 180 ml of filtrate which is referred to as "disintegration phase".

Besides, to the cell pellets resulted from centrifugation were added 30 times volume of 50% methanol and 0.05%(w/v) of TWEEN 20 (polyoxyethylene (20) sorbitan monooleate), and extraction was effected by standing the mixture at room temperature for 3 days. The resulting extract was filtered with an ultrafilter NMWC 10,000 (Whatman) to obtain 120 ml of filtrate which is referred to as "extraction phase".

EXPERIMENTAL EXAMPLE 1

Harmful active oxygen species-scavenging action of the cosmetic material according to the invention In order to evaluate the harmful active oxygen species-scavenging action of the cosmetic material according to the invention, various cosmetic materials were prepared by mixing the disintegration phase and extraction phase, which are obtained in Examples 1 to 3, as shown in Table 1 and tested for their ability of scavenging the superoxide anion radicals using xanthin oxidase by the following method.

Thus, 200 μl of 0.5M potassium phosphate buffer, 100 μl of 16% TRITON X-100 (Sigma), 10 μl of 10 mM ethylenediamine-tetraacetic acid, 300 μl of 1.2 mM neo-tetrazolium chloride and 150 μl of xanthin oxidase (1 unit/nl) were mixed together and 200 μl of each cosmetic material sample shown in Table 1 was added thereto. Superoxide dismutase was employed as a reference material. After adding 100 μl of hypoxanthine and a small amount of water, the mixture was reacted at 37° C. for 20 min. After completion of the reaction, an absorption was measured at 540 nm and the activity of superoxide dismutase which inhibits 50% of the reduction of neo-tetrazolium chloride by superoxide action radicals formed from hypoxanthine by an action of xanthin oxidase was considered as 1 unit. The experiment was carried out twice and the average was calculated. The results are shown in Table 1.

TABLE 1

| Sample (50% dilute) | | | |
|---|---|---|---|
| Example No. | Ratio of disintegration phase to extraction phase | Activity of scavenging superoxide anion radical (%)[a] | Corresponding superoxide dimutase activity (Unit)[b] |
| 1 | 1:1 | 96 | 10 |
|   | 1:2 | 90 | 5 |
|   | 2:1 | 98 | 12 |
| 2 | 1:1 | 90 | 5 |
|   | 1:2 | 85 | 3 |
|   | 2:1 | 93 | 7 |
| 3 | 1:1 | 95 | 9 |
|   | 1:2 | 90 | 5 |
|   | 2:1 | 96 | 10 |

Note:
[a] Inhibition rate of reduction of neotetrazolium chloride
[b] 1 unit corresponds to about 150 ng of superoxide dismutase As shown in Table 1, the cosmetic materials according to the invention show excellent ability of scavenging harmful superoxide anion radicals, and particularly the 2:1 mixtures of disintegration phase and extraction phase show highest inhibition rate of neotetrazolium chloride reduction by superoxide anion radical.

EXPERIMENTAL EXAMPLE 2

DNA repair system-reinforcing action of the cosmetic material according to the invention The DNA repair system-reinforcing action of the cosmetic material according to the invention was evaluated by using the same samples as in Experimental Example 1.

The thymine dimers formed by UV irradiation are repaired by DNA repair systems in living body and, when the DNA repair systems work efficiently, the thymidine uptake increases. The method to evaluate the ability of repairing the DNA by measuring the thymidine uptake is called UDS (Unscheduled DNA Synthesis) method and the DNA repair system-reinforcing action of the samples were tested by the following method.

Thus, keratinocytes collected from the human epithelial cells using a glass coverslip were cultured in KGM medium (Clonetics) for 24 hours. After irradiating the cells with UV light using G15 T8 Germicidal Bulb (Philips) at 10J/$m^2$ for 10 min, 2.5 mM hydroxyurea and 10 μCi/ml $^3$H-thymidine were added and fermentation was carried out for 3 hours. 0.1%, 0.3% or 0.5% of the samples were respectively added while no sample is added to the control. 0.1 mM cold thymidine was added to fix the cells, which were coated with NR-$M_2$ emulsion (Konica). After maintaining at 4° C. for 1 week, the cells were stained with a giemsa solution and the radioactivity was measured by liquid-scintillation spectroscope. UDS is measured by counting the number of grains in 100 (one hundred) non s phase nuclei. Measurement was repeated three times and the average was calculated.

The results are shown in FIG. 1. In FIG. 1, the numerical number 1 indicates 2:1 mixture of the disintegration phase and extraction phase obtained in Example 1, the numerical number 2 indicates 1:1 mixture of the disintegration phase and extraction phase obtained in Example 1, the numerical number 3 indicates 1:2 mixture of the disintegration phase and extraction phase obtained in Example 1, the numerical number 4 indicates 2:1 mixture of the disintegration phase and extraction phase obtained in Example 2, the numerical number 5 indicates 2:1 mixture of the disintegration phase and extraction phase obtained in Example 3 and the numerical number 6 indicates the control having no cosmetic material of the invention.

As shown in FIG. 1, the cosmetic materials according to the invention exhibit excellent property of reinforcing the DNA repair system of the skin.

EXPERIMENTAL EXAMPLE 3

Immune system-reinforcing action of the cosmetic material according to the invention To 96 well plate was distributed 50 μl of anti-human immunoglobulin (Ig) anti-serum (3.5 mg/ml) which was 100 times diluted with 50 mM sodium carbonate buffer (pH 9.0) and the plate was maintained at room temperature for 8 hours. After washing the plate with TBS(Tris Buffered Saline; 10 mM Tris, pH 7.0, 0.15M NaCl) supplemented with 0.01% TWEEN 80 (polyoxyethylene (80) sorbitan monooleate), 100 μl of TBSA(TBS containing 1% bovine serum albumin) was added and the mixture was allowed to stand for 1 hour. 50 μl of B cell culture prepared as described below was added and the mixture was allowed to react for 1 hour. After adding anti-human Ig-horseradish peroxidase which was 1000 times diluted with TBS, the mixture was allowed to react for 1 hours. O-phenylenediamine as a color-developing agent was added and the absorbance at 490 nm was measured. The standard human Ig was employed to obtain the standard curve from which the amount of Ig of the samples was calculated.

Preparation of B cell culture

RPMI 1640 medium (Flow Laboratories) supplemented with 10% fetal calf serum, 50 μg/ml penicillin and 100 μ/ml streptomycin was inoculated with T cells to a concentration of $2\times10^6$ cells/ml and 0.5% of samples obtained in Experimental Example 1 were individually added thereto. Fermentation was carried out at 37° C. for 2 days. The supernatant of the T cell culture was added to a concentration of 10% (v/v) to 10% fetal calf serum medium for B cell cultivation and the cultivation was carried out for 6 days to obtain B cell culture.

Figure 2:
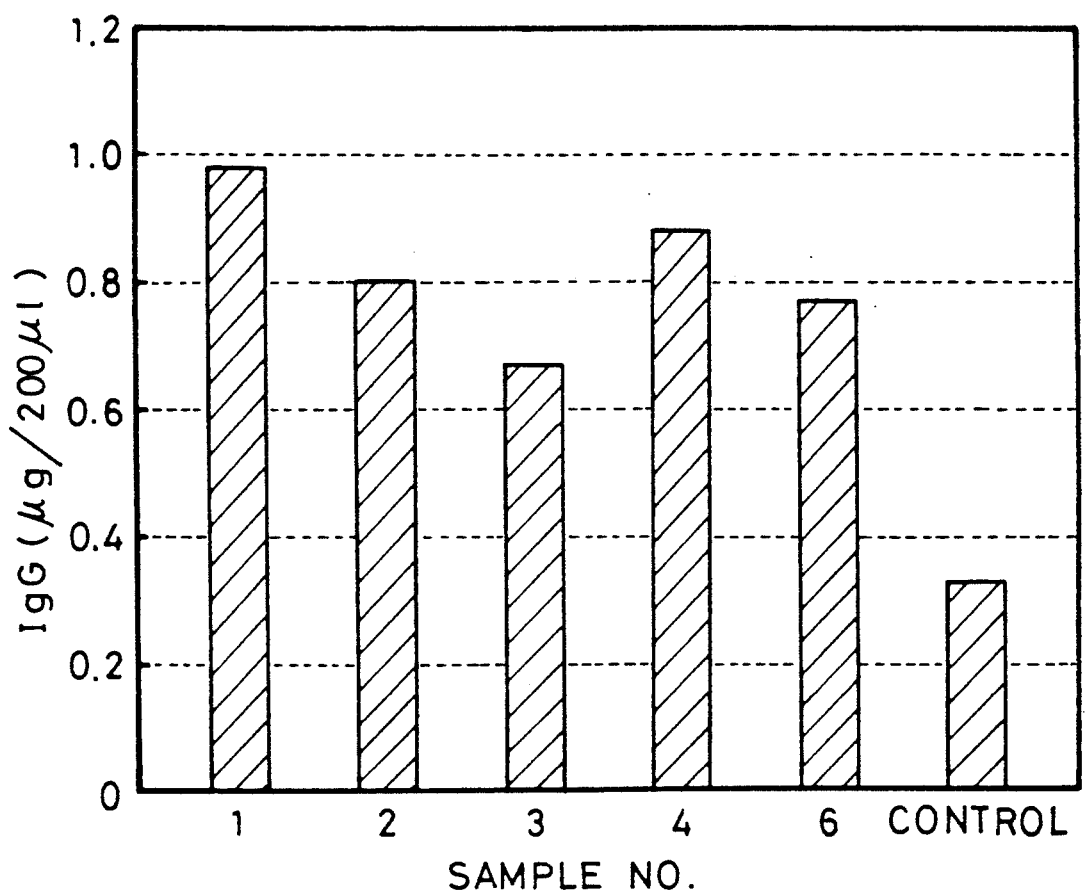
FIG. 2 is a bar graph showing the action of the cosmetic material according to the invention of reinforcing the immune systems of the skin.

The results are shown in FIG. 2. In FIG. 2, the numerical number 1 indicates 2:1 mixture of the disintegration phase and extraction phase obtained in Example 1, the numerical number 2 indicates 1:1 mixture of the disintegration phase and extraction phase obtained in Example 1, the numerical number 3 indicates 1:2 mixture of the disintegration phase and extraction phase obtained in Example 1, the numerical number 4 indicates 2:1 mixture of the disintegration phase and extraction phase obtained in Example 2, the numerical number 5 indicates 2:1 mixture of the disintegration phase and extraction phase obtained in Example 3 and the numerical number 6 indicates the control having no cosmetic material of the invention.

As shown in FIG. 2, the cosmetic materials according to the invention exhibit excellent property of reinforcing the dermal immune system.

What is claimed is:

1. A cosmetic material exhibiting properties of scavenging harmful oxygen species, of reinforcing DNA repair system of the skin and of reinforcing immune system of the skin, which consists of
   (a) a disintegration phase which is obtained by harvesting lactic acid bacterial cells from the lactic fermentation broth, disintegrating the cells, subjecting the broken cells to centrifugation to give a supernatant and adding to the supernatant 10 μM of 500 μM of at least one metal ions followed by filtration to obtain a filtrate and
   (b) an extraction phase which is obtained by extracting cell pellets precipitated by the centrifugation step in (a) with water or an organic solvent and a non-ionic surfactant and subjecting the extract to filtration to obtain a filtrate, and the weight ratio of said integration phase to said extraction phase is 10:1 to 1:10.

2. The cosmetic material according to claim 1, wherein lactic acid bacteria used in the lactic fermentation is selected from the strains of Lactobacillus genus and of Streptococcus genus.

3. The cosmetic material according to claim 1, wherein said metal ions are of bivalent metal ions which are selected from the group consisting of Cu, Fe, Mn, Mg, Zn and Ni, and are employed single or in mixtures thereof.

4. The cosmetic material according to claim 1, wherein said organic solvent is selected from polar organic solvents consisting of methanol and ethanol.

5. The cosmetic material according to claim 1, wherein said filtration is carried out by using an ultrafilter having cut off of 10,000 dalton.

6. The cosmetic material according to claim 1, which further comprises a low molecular weight active oxygen species-scavenger selected from mannitols and flavonoids.

* * * * *